United States Patent
Li et al.

(10) Patent No.: US 10,127,666 B2
(45) Date of Patent: Nov. 13, 2018

(54) MEDICAL INFORMATION PROCESSING APPARATUS, MEDICAL IMAGING DIAGNOSTIC DEVICE, AND METHOD

(71) Applicant: Toshiba Medical Systems Corporation, Otawara-shi (JP)

(72) Inventors: Bing Li, Beijing (CN); Fanjie Meng, Beijing (CN)

(73) Assignee: Toshiba Medical Systems Corporation, Otawara-shi (JP)

( * ) Notice: Subject to any disclaimer, the term of this patent is extended or adjusted under 35 U.S.C. 154(b) by 74 days.

(21) Appl. No.: 15/088,817

(22) Filed: Apr. 1, 2016

(65) Prior Publication Data
US 2016/0292860 A1    Oct. 6, 2016

(30) Foreign Application Priority Data

Apr. 3, 2015 (CN) .......................... 2015 1 0158856
Jan. 21, 2016 (JP) ................................ 2016-010029

(51) Int. Cl.
*G06K 9/00* (2006.01)
*G06T 7/00* (2017.01)
*G06F 19/00* (2018.01)
*A61B 5/05* (2006.01)

(52) U.S. Cl.
CPC .......... *G06T 7/0016* (2013.01); *G06F 19/321* (2013.01); *G06T 2207/10088* (2013.01); *G06T 2207/30004* (2013.01)

(58) Field of Classification Search
USPC ....... 382/100, 103, 128–134, 162, 165, 168, 382/173, 181, 193, 199, 209, 219, 232, 382/254, 274, 276, 286, 294, 305, 312, 382/318; 600/410; 702/19; 435/7.1
See application file for complete search history.

(56) References Cited

U.S. PATENT DOCUMENTS

| | | | |
|---|---|---|---|
| 2009/0030618 A1* | 1/2009 | Cheng ................... | G01R 33/485 702/19 |
| 2010/0329529 A1* | 12/2010 | Feldman .............. | G06K 9/6252 382/131 |
| 2013/0157285 A1* | 6/2013 | Veiseh ..................... | C12Q 1/02 435/7.1 |
| 2013/0267825 A1* | 10/2013 | Wohlgemuth ......... | A61B 5/055 600/410 |
| 2014/0350380 A1* | 11/2014 | Eidelberg ............... | A61B 6/037 600/410 |

FOREIGN PATENT DOCUMENTS

JP    2010-110567    5/2010

* cited by examiner

*Primary Examiner* — Seyed Azarian
(74) *Attorney, Agent, or Firm* — Oblon, McClelland, Maier & Neustadt, L.L.P.

(57) ABSTRACT

A medical information processing apparatus according to an embodiment includes determination circuitry and display control circuitry. The determination circuitry determines whether there is a change in an amount of individual metabolites among a plurality of metabolites in magnetic resonance spectroscopy within a part worthy of attention set on medical image data by comparing the amount of each of the plurality of metabolites with a reference value corresponding to each metabolite. The display control circuitry display identification information by associating therewith the part worthy of attention, the identification information identifying whether the amount of each of the plurality of metabolites is changed.

19 Claims, 10 Drawing Sheets

MEDICAL INFORMATION PROCESSING APPARATUS, MEDICAL IMAGING DIAGNOSTIC DEVICE, AND METHOD

CROSS-REFERENCE TO RELATED APPLICATIONS

This application is based upon and claims the benefit of priority from Chinese Patent Application No. 201510158856.6, filed on Apr. 3, 2015; and Japanese Patent Application No. 2016-010029, filed on Jan. 21, 2016, the entire contents of all of which are incorporated herein by reference.

FIELD

The present invention relates generally to the medical image processing field and more particularly to a data processing apparatus and a data processing method for processing medical image data rapidly and automatically and a medical imaging device.

BACKGROUND

With the development of medical imaging technologies, the application of medical imaging devices has been popularized. As a huge amount of information is contained in an image obtained using a medical imaging device, a specialized person such as a doctor needs to extract a plurality of voxels from a target region of the observed object, check the obtained data voxel by voxel and empirically determine, for example, whether or not there is a voxel which may have abnormality, based on the data. This approach which requires voxels to be operated one by one is incapable of rapidly and efficiently recognizing a voxel which is significantly changed when compared with a normal one and the degree of the change and may miss a voxel which is not expected to have abnormality. Further, as the determination is merely based on personal experience, the result may be inaccurate.

Therefore, a technology is desired by means of which a significantly changed voxel can be automatically recognized rapidly and accurately to find a part worthy of attention for a further examination. Moreover, it is also expected to track the condition of the same part of the same patient and compare the conditions using this technology.

BRIEF DESCRIPTION OF THE DRAWINGS

The present invention will be better understood with reference to the following description when taken in conjunction with accompanying drawings in which identical or like reference signs denote identical or like components. The accompanying drawings, together with the detailed description below, are incorporated into and form a part of the specification and serve to illustrate, by way of example, preferred embodiments of the present invention and to explain the principle and advantages of the present invention. In the accompanying drawings.

DETAILED DESCRIPTION

The following presents a simplified summary of the present invention to provide a basic understanding of some aspects of the present invention. It should be appreciated that the simplified summary, which is not the exhaustive overview of the present invention, is not intended to identify the key or critical parts of the present invention or limit the scope of the present invention, but merely to present some concepts in a simplified form as a prelude to the more detailed description that is presented later.

A medical information processing apparatus according to an embodiment includes determination circuitry and display control circuitry. The determination circuitry determines whether there is a change in an amount of individual metabolites among a plurality of metabolites in magnetic resonance spectroscopy within a part worthy of attention set on medical image data by comparing the amount of each of the plurality of metabolites with a reference value corresponding to each metabolite. The display control circuitry display identification information by associating therewith the part worthy of attention, the identification information identifying whether the amount of each of the plurality of metabolites is changed.

In accordance with an aspect of the present invention, a data processing apparatus is provided which includes: a data loading unit configured to load data of one or more voxels obtained by scanning a specific part of an object body; a change detection unit configured to detect, by performing a comparison using a characteristic parameter obtained from the data, a voxel undergoing a change which refers to that the difference of the characteristic parameter and a reference value exceeds a predetermined degree; and a change presentation unit configured to indicate a position of the voxel undergoing the change and a degree of the change to a user through a display. Here, it should be noted that the data processing apparatus is an example of a medical information processing apparatus.

In accordance with another aspect of the present invention, a medical imaging device is provided which comprises the foregoing data processing apparatus. Here, it should be noted that the medical imaging device is an example of a medical imaging diagnostic device.

In accordance with still another aspect of the present invention, a data processing method is provided which comprises: loading data of one or more voxels obtained by scanning a specific part of an object body; detecting, by performing a comparison using a characteristic parameter obtained from the data, a voxel undergoing a change which refers to that the difference of the characteristic parameter and a reference value exceeds a predetermined degree; and indicating a position of the voxel undergoing the change and a degree of the change to a user through a display. Here, it should be noted that the data processing method is an example of a method for processing medical information.

Further, in accordance with yet another aspect of the present invention, a computer program for realizing the foregoing data processing method is provided. In this aspect of the present invention, for example, a program for processing medical information is provided as a computer program.

Further, in accordance with yet still another aspect of the present invention, a computer program product at least in a computer-readable medium form is provided on which computer program codes for realizing the foregoing data processing method are recorded.

In the data processing method, the data processing apparatus and the data image device of the present invention, by automatically detecting a changed voxel through the synchronous loading of the scanned data of a plurality of voxels and a subsequent comparison, a part worth of attention is found for further examination. In this way, a changed voxel can be recognized rapidly, efficiently and accurately.

Embodiments of the present invention are described below with reference to accompanying drawings. The elements and features described in an accompanying drawing or embodiment of the present invention can be combined with those shown in one or more other accompanying drawings or embodiments. It should be noted that for the sake of clarity, representation and description of the components and processing that are unrelated to the present invention but well known to those of ordinary skill in the art are omitted in accompanying drawings and description.

Figure 1:
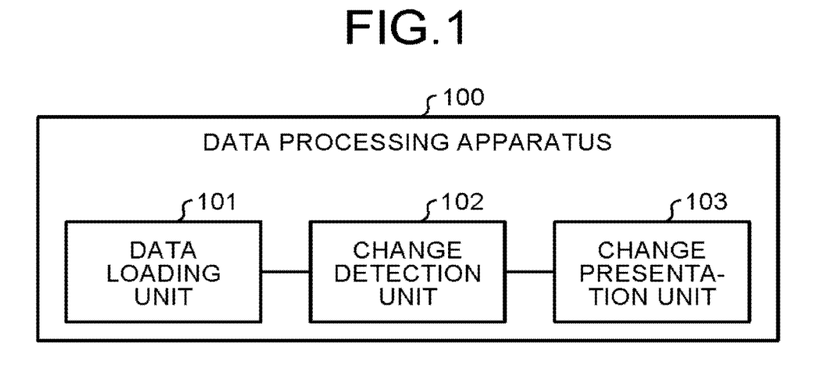
FIG. 1 is a block diagram illustrating the structure of a data processing apparatus according to an embodiment of the present invention.

FIG. 1 is a block diagram illustrating the structure of a data processing apparatus 100 according to an embodiment of the present invention, and as shown in FIG. 1, the data processing apparatus 100 for processing medical image data includes: a data loading unit 101 configured to load data of one or more voxels obtained by scanning a specific part of an object body; a change detection unit 102 configured to detect, by performing a comparison using a characteristic parameter obtained from the data, a voxel undergoing a change which refers to that the difference of the characteristic parameter and a reference value exceeds a predetermined degree; and a change presentation unit 103 configured to indicate a position of the voxel undergoing the change and a degree of the change to a user through a display. The excess in the difference between the characteristic parameter and the reference value over the predetermined degree is referred to as "change" or "abnormal (abnormality)" in the present embodiment.

In the description of embodiments of the present invention, the image data of one or more voxels is obtained by scanning a specific part of an object body using a medical imaging device. Scan may be single-voxel scan or multi-voxel scan, depending on the number of the voxels scanned at a time. However, it should be appreciated that in the adoption of single-voxel scan, to scan a plurality of voxels, it is needed to carry out the scan operation for many times and to store the scanned data separately, while in the adoption of multi-voxel scan, a plurality of voxels can be scanned and data can be stored through one single scan operation.

The data loading unit 101 loads data obtained in this way for subsequent processing. Specifically, the data loading unit 101 may load the data of a plurality of voxels which are stored separately or together and which seem to belong to the same group. As there is no need to, for example, manually load the scanned data of a plurality of individual voxels, the processing efficiency can be improved.

The scanned object may be a people or an animal, and the specific part of the body includes but apparently is not limited to: brain, lung, heart, liver, kidney and other organs or tissues. The medical imaging device, which is also referred to a medical diagnostic device, includes, but is not limited to: an X-ray imaging diagnostic device, an Ultrasound (UL) diagnostic imaging device, a Computed Tomography (CT) device, a Magnetic Resonance Imaging (MRI) device, a Positron Emission Tomography (PET) device and so on.

After the data is loaded, the change detection unit 102 can obtain a related characteristic parameter from the data and finds a changed voxel by performing a comparison using the characteristic parameter. Specifically, for each voxel, the characteristic parameter has a reference value, and if the difference between the characteristic parameter obtained and the reference value exceeds a certain degree, then the voxel is changed. In other words, the change detection unit 102 which serves as a determination circuitry determines whether there is a change in an amount of individual metabolites among a plurality of metabolites in magnetic resonance spectroscopy within a part worthy of attention set on the medical image data by comparing the amount of each of the plurality of metabolites with a reference value corresponding to each metabolite.

Subsequently, the change presentation unit 103 indicates the position of the changed voxel to the user through a display and may indicate the degree of the change at the same time, thus saving the time spent on determining the position of the most serious voxel in a case where there are a plurality of voxels. The degree of the change can be defined by the mean and the variance of the characteristic parameter. In other words, the change presentation unit 103 which serves as a display control circuitry displays identification information by associating therewith the part worthy of attention, the identification information identifying whether or not the amount of each of the plurality of metabolites is changed.

In an embodiment, the reference value includes at least one of: an empirical value, the corresponding value of a symmetric voxel and a historical value of the symmetric voxel. That is, the reference value (corresponding to each metabolite) is at least one of the empirical value that is empirically obtained, the corresponding value corresponding to a region symmetrical in position to the part worthy of attention, and the historical value that is previously obtained.

Figure 2:
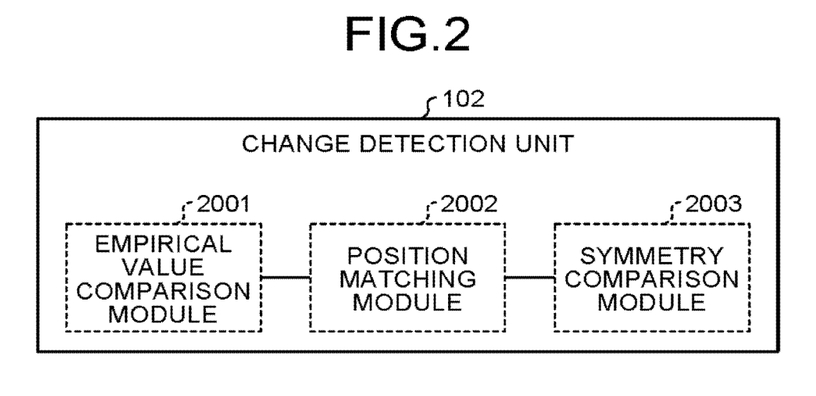
FIG. 2 is an exemplary block diagram illustrating the structure of a change detection unit in a data processing apparatus according to an embodiment of the present invention.

FIG. 2 is an exemplary block diagram illustrating the structure of the change detection unit 102 in the data processing apparatus 100 according to an embodiment of the present invention. Based on previous experience, the extracted characteristic parameter has a certain value or a value varying within a certain range under normal circumstances, thus, the change detection unit 102 may include an empirical value comparison module 2001 which, as shown in FIG. 2, is configured to compare the obtained characteristic parameter with a preset empirical value.

In an embodiment, the empirical value is related to at least one of the specific part, a scanning sequence, the race of the object and the age of the object and is obtained from a pre-trained database. The empirical value may also be an empirically obtained threshold.

Further, as a human body or an animal body is generally symmetrical (e.g., bilaterally symmetrical), whether or not a voxel is changed can be determined by comparing corresponding characteristic parameters of two voxels which are symmetrical in position. As shown in FIG. 2, the change detection unit 102 may further include: a position matching module 2002 configured to obtain, aiming at a voxel, a voxel symmetrical in position to the voxel; and a symmetry comparison module 2003 configured to compare characteristic parameters of the two voxels to determine whether or not one of the voxels is changed. Specifically, an automatic position matching operation is performed on two individual voxels, characteristic parameters of two successfully matched voxels are compared, and it is determined that one of the voxels is changed when the result of the comparison shows, for example, a relatively great difference between the characteristic parameters of the two voxels. It should be noted that in FIG. 2, each module is represented by dotted lines, which means the modules are optional.

The obtained characteristic parameter may also be compared with historical values to determine whether or not a change occurs. How to compare the obtained characteristic parameter with historical values is described below in detail with reference to FIG. 3 to FIG. 5.

Figure 3:
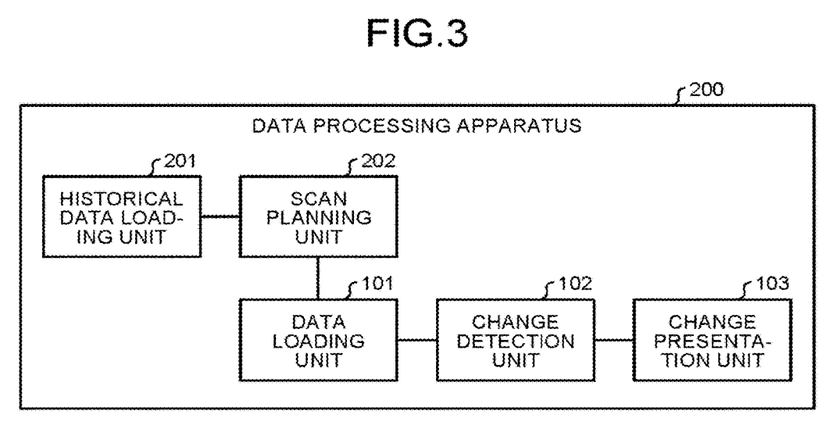
FIG. 3 is a block diagram illustrating the structure of a data processing apparatus according to another embodiment of the present invention.

FIG. 3 is a block diagram illustrating the structure of a data processing apparatus 200 according to another embodiment of the present invention. As shown in FIG. 3, in addition to the data loading unit 101, the change detection unit 102 and the change presentation unit 103, the data processing apparatus 200 further includes: a historical data loading unit 201 configured to load the historical data of a voxel stored aiming at a specific part of the same object body; and a scan planning unit 202 configured to set the position to be scanned currently and scanning parameters according to the historical data, wherein the current data loaded by the data loading unit 101 is obtained by scanning the specific part of the object body according to the position to be scanned and the scanning parameters.

By including the historical data loading unit 201 and the scan planning unit 202, the data processing apparatus 200 can perform the current scan by finding a voxel the same as a historically scanned one to obtain the change of a characteristic parameter of the voxel with time, which greatly help a doctor accurately know the development of a disease in the case of, for example, periodic checkups.

The historical data may be stored in a storage device arranged in or attached to the data processing apparatus 200. The storage device includes a computer-readable storage medium which is, for example (but not limited to), an electrical system, device or apparatus, a magnetic system, device or apparatus, an optical system, device or apparatus, an electromagnetic system, device or apparatus, an infrared system, device or apparatus, a semiconductor system, device or apparatus or any proper combination thereof. More specific examples (a non-exhaustive list) of the computer-readable medium include: an electrical connection having one or more wires, a portable computer disk, a hard disk, a Random Access Memory (RAM), a Read-Only Memory (ROM), an Erasable Programmable Read-Only Memory (EPROM or Flash memory), an optical fiber, a portable Compact Disc Read-Only Memory (CD-ROM), an optical storage device, a magnetic storage device or any proper combination thereof. On the other hand, the historical data may also be obtained from a network such as the Internet or a local area network through wired or wireless communication.

After the historical data is obtained, the scan planning unit 202 obtains, according to the historical data, the position to be scanned corresponding to historical scans and scanning parameters used in historical scans, in other words, the scan planning unit restores the object and the conditions of historical scans as best as possible.

Figure 4:
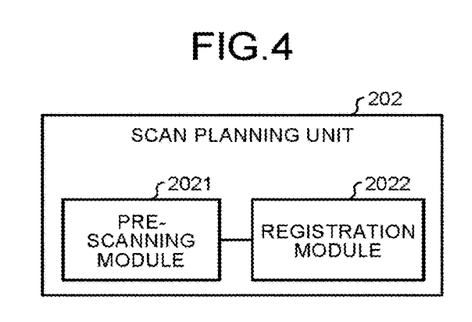
FIG. 4 is an exemplary block diagram illustrating the structure of a scan planning unit in a data processing apparatus according to another embodiment of the present invention.

FIG. 4 is an exemplary block diagram illustrating the structure of the scan planning unit 202 in the data processing apparatus 200 according to an embodiment of the present invention. As shown in FIG. 4, the scan planning unit 202 may include: a pre-scanning module 2021 configured to pre-scan the object body to obtain a scan location map; and a registration module 2022 configured to perform a registration on the scan location map and the historical data to unify the position to be scanned currently and the scanned position in the historical data.

The pre-scanning module 2021 performs the pre-scanning very rapidly because the pre-scanning is merely performed to obtain a scan location map representing the structure of a human body. With the use of the registration module 2022, the part to be scanned can be found rapidly using the historical data, thus saving time and improving the accuracy of the comparison. The registration can be carried out using any existing registration technology. For example, the position to be scanned which is equivalent to the scanned position in the historical data can be shown in the scan location map along with an image resulting from the pre-scanning, and this process can be carried out automatically. Moreover, preferably, when applied to magnetic resonance imaging, the data processing apparatus may present the degrees of the changes of a plurality of metabolites with the darkness of colors, as described later, at a shown scanned position and may further present the change trends of the degrees of the changes of the metabolites with time.

Figure 5:
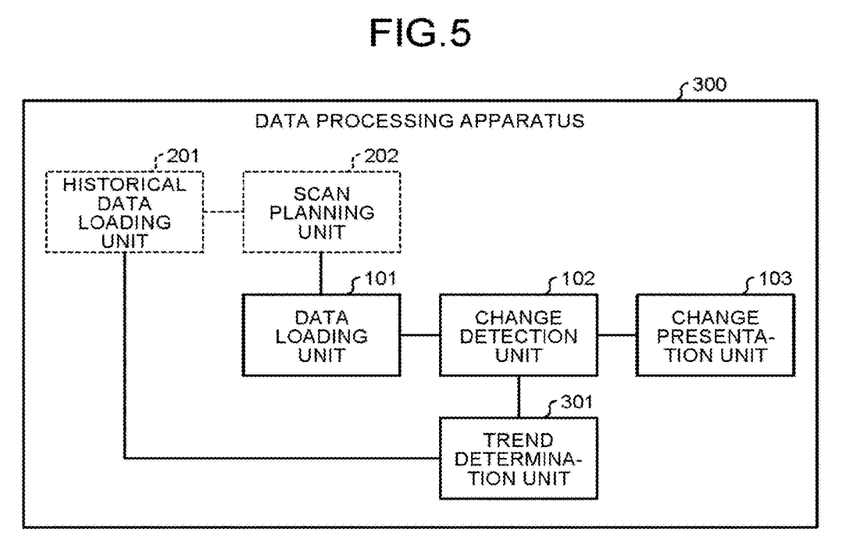
FIG. 5 is a block diagram illustrating the structure of a data processing apparatus according to still another embodiment of the present invention.

FIG. 5 is a block diagram illustrating the structure of a data processing apparatus 300 according to still another embodiment of the present invention. As shown in FIG. 5, in addition to the data loading unit 101, the change detection unit 102 and the change presentation unit 103 described with reference to FIG. 1 and the historical data loading unit 201 and the scan planning unit 202 described with reference to FIG. 3, the data processing apparatus 300 further includes a trend determination unit 301 configured to determine the change trend of the characteristic parameter of each voxel with time based on the current data loaded by the data loading unit 101 and the historical data. With the data processing apparatus 300, the change of the condition of each voxel with time can be observed accurately to provide a diagnosis or treatment reference for a doctor.

Figure 6:
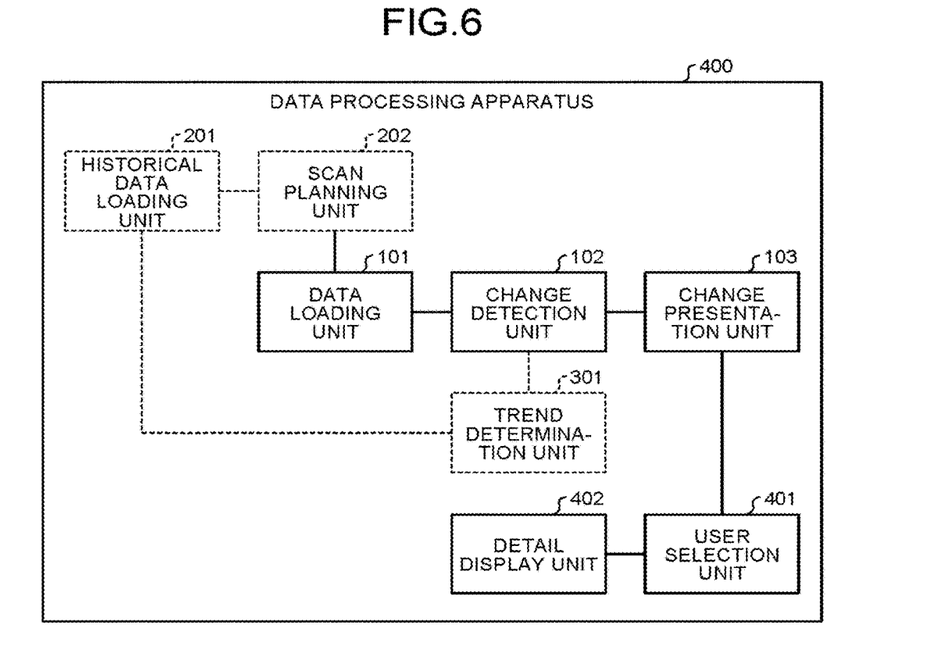
FIG. 6 is a block diagram illustrating the structure of a data processing apparatus according to yet another embodiment of the present invention.

Additionally, FIG. 6 is a block diagram illustrating the structure of a data processing apparatus 400 according to still another embodiment of the present invention. As shown in FIG. 6, in addition to the data loading unit 101, the change detection unit 102 and the change presentation unit 103 described with reference to FIG. 1, the historical data loading unit 201 and the scan planning unit 202 described with reference to FIG. 3 and the trend determination unit 301 described with reference to FIG. 5, the data processing apparatus 400 can further include: a user selection unit 401 configured to select one or more voxels through an input of the user; and a detail display unit 402 configured to display information related to the characteristic parameter of the one or more selected voxels. It should be noted that the modules represented by dotted lines in FIG. 6 are optional.

For example, after changed voxels are determined, one of the changed voxels may be selected to specifically check a characteristic parameter of the selected voxel or related information obtained based on the characteristic parameter of the selected voxel such as the comparison with an empirical value or the value of a symmetrical voxel. Such information can be displayed in the form of, for example, a table or a graph. It should be appreciated that the user can selectively check an unchanged voxel. In an embodiment, the user can select a desired voxel using a mouse, a keyboard, a voice input device and the like.

As an example, Magnetic Resonance Spectroscopy (MRS), which is carried out by a Magnetic Resonance Imaging (MRI) device including the foregoing data processing apparatus 100, 200, 300 or 400, has been widely applied as a noninvasive analysis technology for studying the change of metabolites in the human body. In magnetic resonance spectroscopy, a post-processing, for example, a chemical-shift imaging, is performed on the measurement result of a metabolite to obtain a spectral line chart and the concentration of the metabolite.

In the example, the characteristic parameter includes at least one of: the metabolic concentration of the metabolite, the peak height of the spectral line of the metabolite and relative values to metabolic concentrations of other metabolites or relative values to the peak heights of spectral lines of other metabolites. Taking the scan on a brain as an example, the metabolites focused on include: NAA, choline, inositol, total creatine and the like, for example.

It should be appreciated that the application range of the present invention is not limited to MRS and the characteristic parameter is not limited to the foregoing example which is merely given for the purpose of illustration but not limitation. Each embodiment of the present invention can be modified appropriately to be adaptive to various other applications.

In the data processing apparatus provided herein, the change presentation unit 103 may be configured to indicate the degree of a change using the darkness of a color and indicate different metabolites using different colors if there are characteristic parameters of a plurality of metabolites so that the user can observe the degree of the change of a voxel and the type of the change more intuitively.

For example, the change detection unit 102 compares the amount (e.g. metabolic concentration, the peak height of the spectral line) of a metabolite measured through MRS or the ratio of the metabolite to a plurality of metabolites with the normal range of an empirical value or the corresponding value or a historical value of a symmetrical voxel to determine whether or not the value of the metabolite is abnormal, wherein the specific part, a scanning sequence, the race and the age of the object and other factors may be taken into consideration during the determination. The change presentation unit 103 presents the metabolite the value of which is determined abnormal as a chart or a color mapping.

As an example, the change presentation unit 103 may further present lines representing the position and the shape of a voxel on an image (e.g. MRI image) resulting from a scan, segment each voxel into a plurality of regions (for example, nine grids) and present the degree of the change of corresponding metabolite with different colors in different regions. In this way, the degrees of the changes of a plurality of metabolites in one or more voxels can be presented at the same time. Further, the change presentation unit 103 may be further configured to present a characteristic parameter of a metabolite and the degree of the change of the metabolite in each region. The presentation mode of the change presentation unit 103 can be set according to the actual needs.

The change presentation unit 103 may further present explanatory notes (legends) representing the correspondence relationship between colors and metabolites, for example, the representation of NAA by a series of red colors, the representation of choline by a series of green colors, the representation of inositol by a series of purple colors and the representation of total creatine by a series of yellow colors. A darker color represents a higher degree of change in a corresponding metabolite. The explanatory notes (legends) may be presented at a fixed position (e.g. the right-upper corner) in an image or a position which is not so critical.

As stated above, by using the data processing apparatus 100, 200, 300 or 400 disclosed herein, a changed voxel and the degree of the change of the voxel can be found automatically, rapidly and accurately to find a part worthy of attention for further examination, thus improving the efficiency of recognition.

Apparently, some processing or methods are also disclosed during the process of describing the data processing apparatus disclosed herein. These methods are summarized below without repeatedly describing the details which have been discussed above. However, it should be appreciated that these methods, although disclosed during the process of describing the data processing apparatus, do not necessarily employ the foregoing components or are not necessarily executed by the foregoing components. For example, embodiments of the data processing apparatus may be partially or totally implemented as hardware and/or firmware, and the data processing method discussed below may also be wholly implemented as a computer-executable program, though these methods can also be implemented as hardware and/or firmware of the data processing apparatus.

Figure 7:
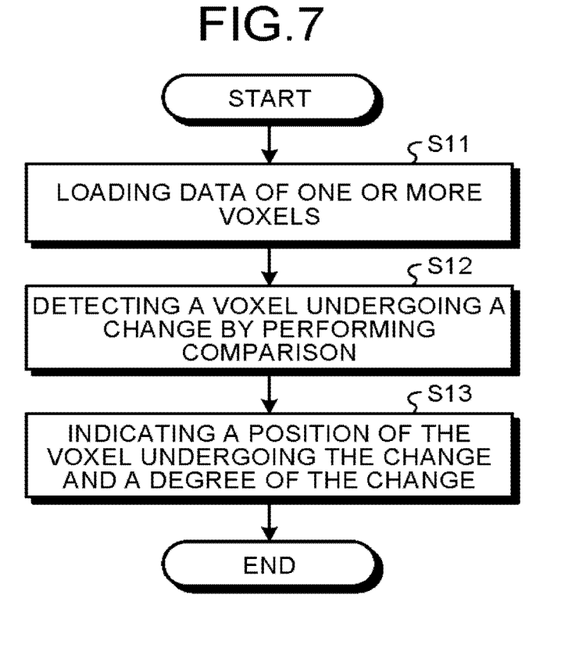
FIG. 7 is a flowchart schematically illustrating a data processing method according to an embodiment of the present invention.

FIG. 7 is a flowchart schematically illustrating a data processing method according to an embodiment of the present invention. The data processing method includes: loading data of one or more voxels obtained by scanning a specific part of an object body (S11); detecting, by performing a comparison using a characteristic parameter obtained from the data, a voxel undergoing a change which refers to that the difference of the characteristic parameter and a reference value exceeds a predetermined degree (S12); and indicating a position of the voxel undergoing the change and a degree of the change to a user through a display (S13).

The reference value includes at least one of: an empirical value, the corresponding value of a symmetric voxel and a historical value of the symmetric voxel. Accordingly, the comparison carried out in step S12 includes comparing the obtained characteristic parameter with a preset empirical value. The empirical value may be an empirical threshold. Alternatively, the empirical value is related to at least one of the specific part, a scanning sequence, the race of the object and the age of the object and is obtained from a pre-trained database.

In an embodiment, a changed voxel may also be detected in the following way: aiming at a voxel, a voxel symmetrical in position to the voxel is obtained, and characteristic parameters of the two voxels are compared to determine whether or not one of the two voxels is changed. This approach is based on the principle that a human body is substantially a symmetrical structure.

Figure 8:
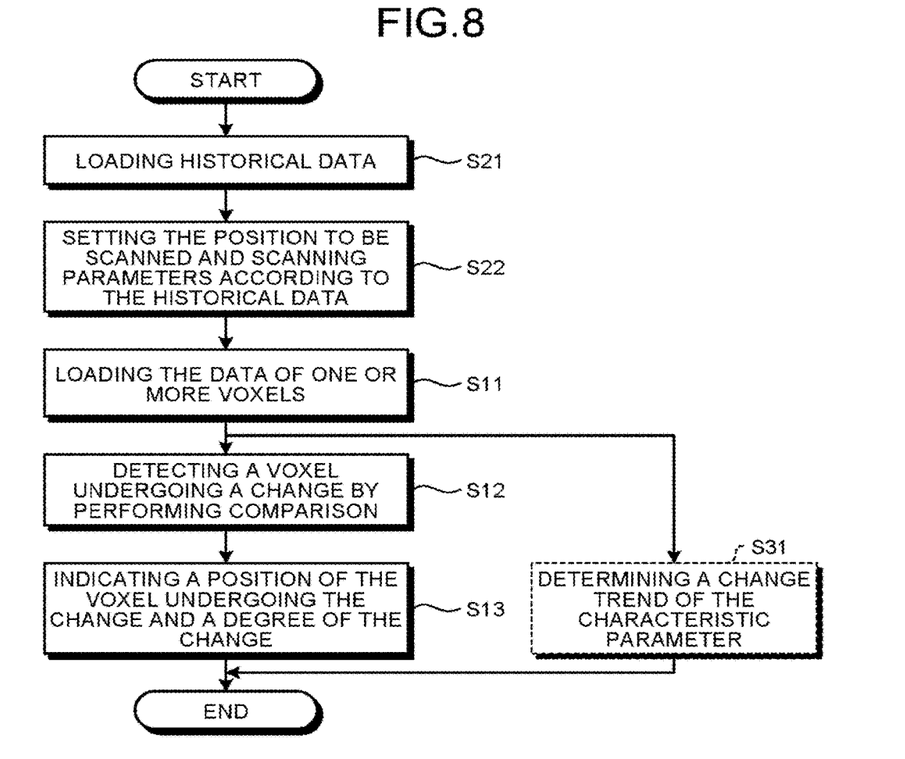
FIG. 8 is a flowchart schematically illustrating a data processing method according to another embodiment of the present invention.

FIG. 8 is a flowchart schematically illustrating a data processing method according to another embodiment of the present invention. Apart from steps S11-S13 described with reference to FIG. 7, the data processing method further includes, before step S11, loading historical data of a voxel stored aiming at a specific part of the same object body (S21) and setting the position to be scanned currently and scanning parameters according to the historical data, wherein the current data loaded is obtained by scanning the specific part of the object body according to the scanned position and the scanning parameters. By including the two steps, the data processing method realizes the consistency of the acquisition of scanned data so that the change in the condition of the same voxel can be accurately compared and analyzed.

Additionally, the data processing method shown in FIG. 8 further includes a step (framed by dotted lines) of determining the change trend of a characteristic parameter of each voxel with time based on the current data loaded and the historical data (S31).

Figure 9:
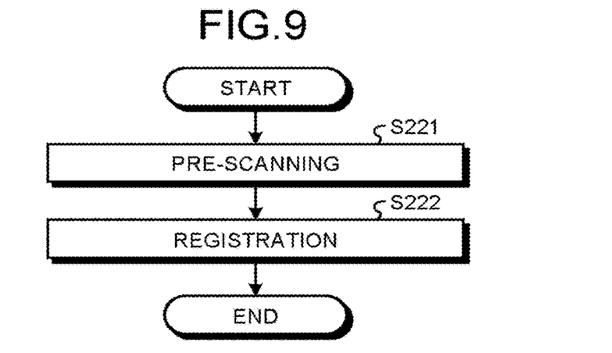
FIG. 9 is a flowchart schematically illustrating sub-steps of step S22 shown in FIG. 8.

FIG. 9 is a flowchart schematically illustrating sub-steps of step S22 shown in FIG. 8. As shown in FIG. 9, step S22 may include the following sub-steps: pre-scanning the object body to obtain a scan location map (S221); and performing a registration on the scan location map and the historical data to unify the position to be scanned and the scanned position in the historical data (S221). It should be appreciated that step S221 can be executed using any existing technology.

Figure 10:
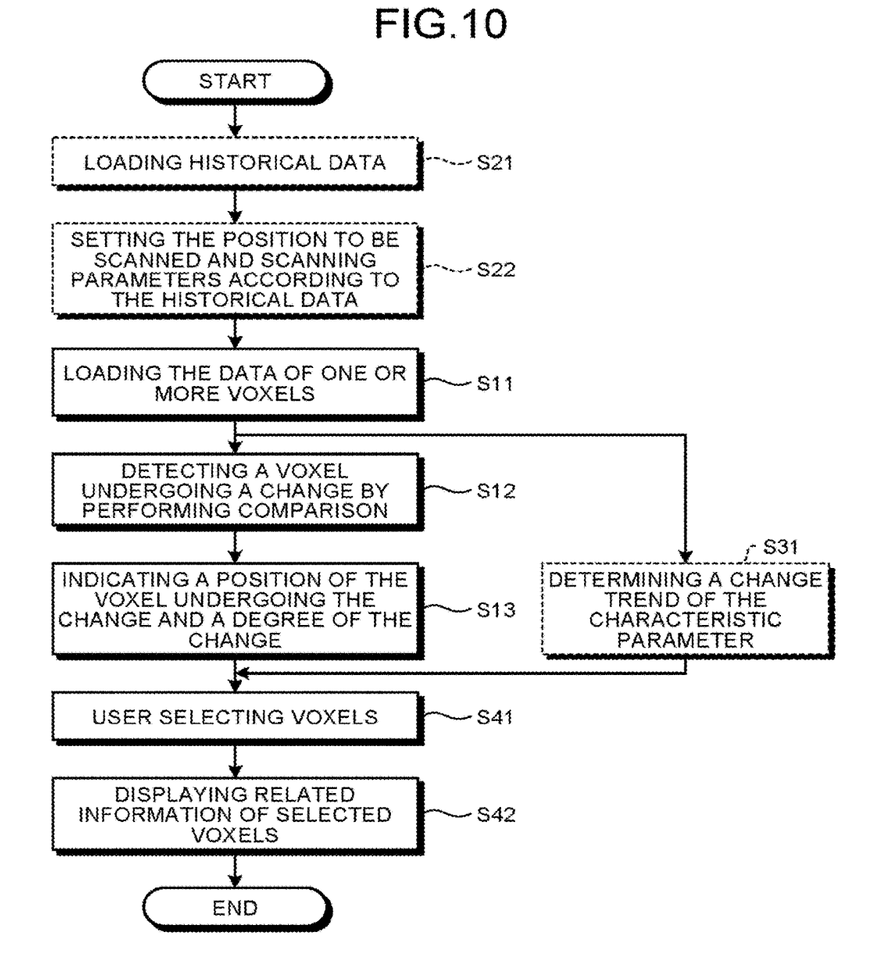
FIG. 10 is a flowchart schematically illustrating a data processing method according to still another embodiment of the present invention.

FIG. 10 is a flowchart schematically illustrating a data processing method according to still another embodiment of the present invention. In addition to steps S11-S13, the data processing method further includes: selecting one or more voxels through the input of the user (S41); and displaying information related to the characteristic parameter of the one or more selected voxels (S42). The method may further include steps S21-S22 or steps S21-S22 and step S31 which are framed by dotted lines.

As a non-limiting example, the characteristic parameter can include at least one of: the metabolic concentration of a metabolite, the peak height of the spectral line of the metabolite and relative values to metabolic concentrations of other metabolites or relative values to the peak heights of spectral lines of other metabolites. These parameters may be obtained through magnetic resonance spectroscopy. It should be appreciated that the method for obtaining these parameters is not limited to the exemplary one which is merely described here for illustrative purpose.

In each of the foregoing embodiments, the degree of a change can be defined by the mean and the variance of a characteristic parameter.

In an embodiment, the degree of a change is indicated using the darkness of a color in step S13, and different metabolites are separately indicated using different colors if there are characteristic parameters of a plurality of metabolites. In this way, a more visualized display is provided.

Figure 11:
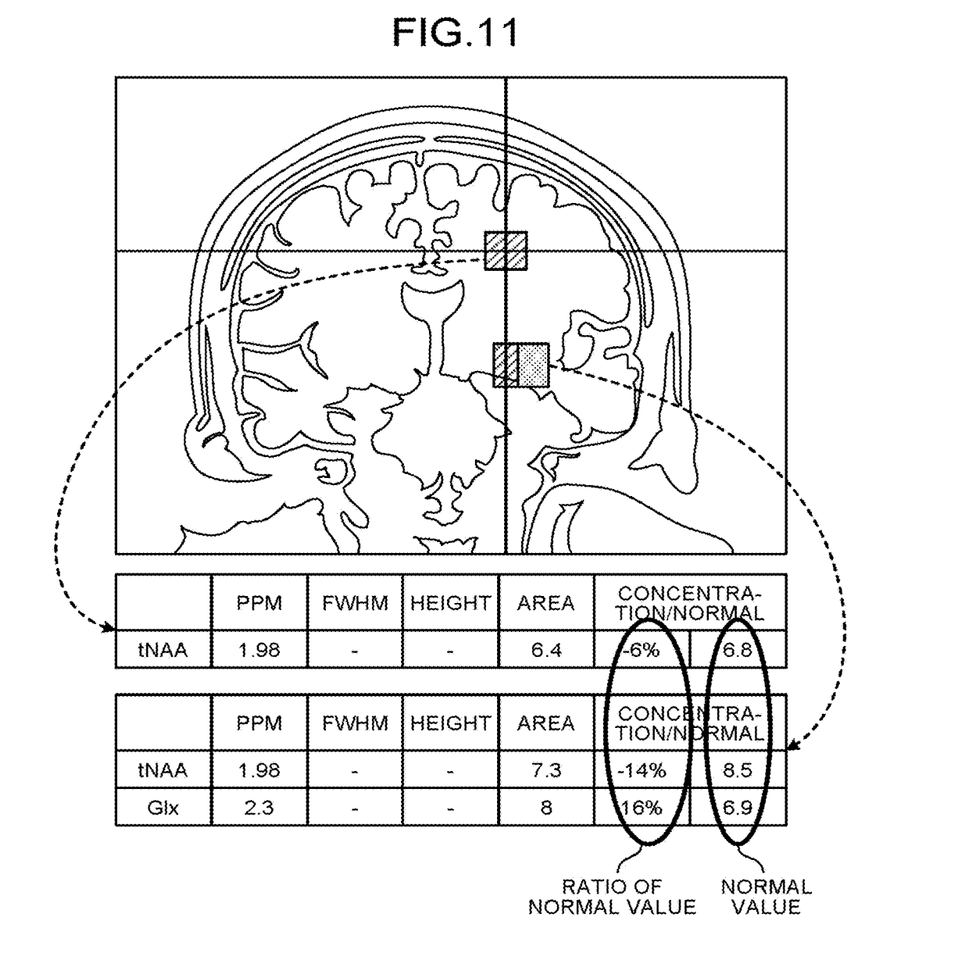
FIG. 11 is a diagram illustrating an application example of a data processing apparatus 100 according to an embodiment of the present invention.
Figure 12:
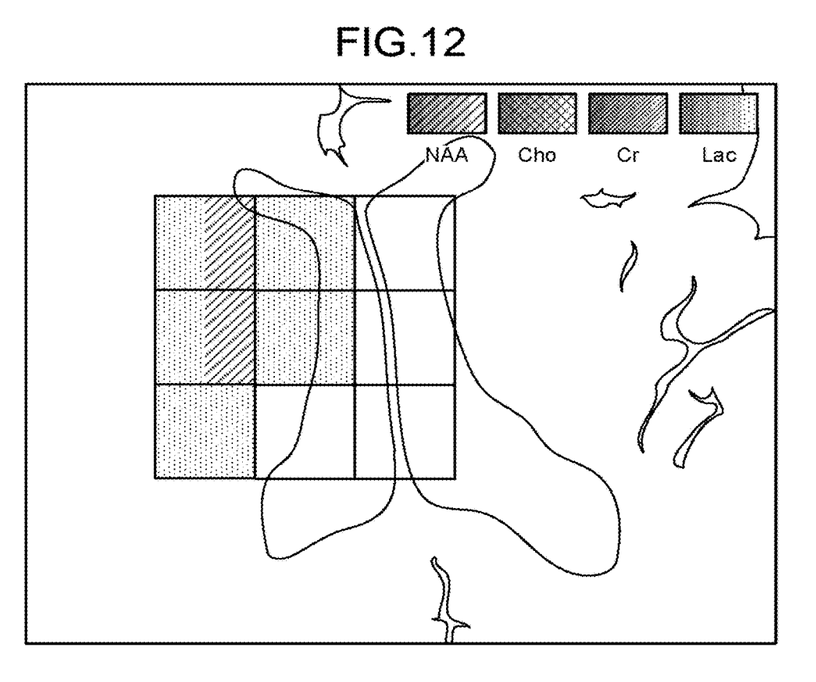
FIG. 12 is a diagram illustrating the application example of the data processing apparatus 100 according to an embodiment of the present invention.

An application example of the above embodiment will now be described. FIGS. 11 and 12 are diagrams illustrating an application example of the data processing apparatus 100 according to the embodiment. FIGS. 11 and 12 illustrate a display screen of the data processing apparatus 100 according to the embodiment, by way of example.

As shown in FIG. 11, for example, the change presentation unit 103 presents a medical image of a head (brain) of an object body and two lists. Here, the lists are provided to present information on metabolites within the part worthy of attention set on the medical image. In an example of FIG. 11, the upper list presents information corresponding to the upper part of the part worthy of attention and the lower list presents information corresponding to the lower part of the part worthy of attention.

For example, the change presentation unit 103 presents information on tNAA as a metabolite in the upper list. In particular, the change presentation unit 103 establishes association among ppm (concentration), FWHM (full width half maximum), height (peak value of a spectrum), area, and Concentration/Normal (ratio of concentration of a metabolite to the corresponding average concentration) of tNAA based on magnetic resonance spectroscopy within the part worthy of attention, in presentation. The change presentation unit 103 presents the part worthy of attention with a color corresponding to the ratio of concentration of tNAA to the average concentration thereof. In particular, the change detection unit 102 compares the ratio of concentration of tNAA to the average concentration thereof with the reference value (e.g., any threshold) to determine whether or not the ratio of concentration of tNAA to the average concentration thereof is changed. The change presentation unit 103 then presents the part worthy of attention with a color corresponding to the determination made by the change detection unit 102. For example, if the ratio of concentration of tNAA to the average concentration thereof is changed, the part worthy of attention is colored in "red", and if not, in "blue."

Further, the change presentation unit 103 presents, for example, information on tNAA and Glx as metabolites in the lower list. In particular, the change presentation unit 103 establishes association among ppm (concentration), FWHM (full width half maximum), height (peak value of the spectrum), area, and Concentration/Normal (ratio of concentration of metabolites to the corresponding average concentration) with respect to tNAA and Glx based on magnetic resonance spectroscopy within the part worthy of attention, in presentation. The change presentation unit 103 presents the part worthy of attention with a color corresponding to the ratio of concentration of the metabolites to the average concentration thereof. The lower list contains information on two metabolites. In this case, the change presentation unit 103 presents determination individually made with respect to tNAA and Glx. In an example of FIG. 11, the change presentation unit 103 presents a color corresponding to the determination made for tNAA on the left side of the part worthy of attention, and a color corresponding to the determination made for Glx on the right side of the part worthy of attention.

Still further, the change presentation unit 103 presents, for example, the degree of a change by shades of a color, as shown in FIG. 12. For example, the change detection unit 102 determines whether or not the ratio of concentration of each of NAA, Cho, Cr, and Lac to the corresponding average concentration is changed, and if so, determines the degree of the change. The change detection unit 102 determines, for example, the degree of the change in accordance with the difference between the ratio of concentration of each metabolite to the corresponding average concentration and the threshold. The change presentation unit 103 then presents each of NAA, Cho, Cr, and Lac in darker shading as the difference between the ratio of concentration of each metabolite to the corresponding average concentration and the threshold increases. If a change is not found in the ratio of concentration of each metabolite to the corresponding average concentration, the part worthy of attention is not colored.

More specific details of each step and more possible steps of the foregoing data processing method may be understood with reference to the description on each component in the data processing apparatus disclosed herein and are therefore not described here repeatedly.

Figure 13:
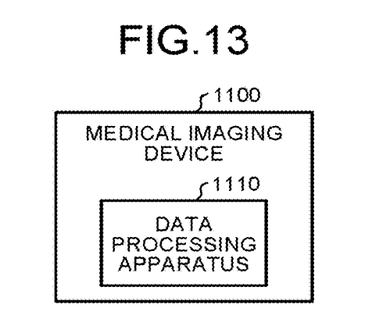
FIG. 13 is a block diagram schematically illustrating a medical imaging device according to an embodiment of the present invention.

FIG. 13 is a block diagram schematically illustrating a medical imaging device according to an embodiment of the present invention. In order not to obscure the spirit and scope of the present invention, other possible members of the medical imaging device are omitted in FIG. 13. The medical imaging device 1100 includes a data processing apparatus 1110 for automatically detecting a changed voxel and presenting the position of the changed voxel and the degree of the change of the voxel to the user. The data processing apparatus 1110 may be any of the data processing apparatuses 100, 200, 300 and 400 described in the foregoing embodiments. The medical imaging device 1100, to which no limitations are given, may be, for example, an X-ray imaging diagnostic device, an UL diagnostic imaging device, a CT device, an MRI device, a PET device or the like.

The specific way or manner in which the foregoing data processing apparatus is arranged in a medical imaging device is well known to those skilled in the art and is therefore not described repeatedly here.

As an example, each step of the foregoing data processing method and each module and/or unit of the foregoing data processing apparatus may be implemented as software, firmware, hardware or a combination thereof. In a case where steps or modules and/or units are achieved through software or firmware, programs constituting software for realizing the foregoing method may be installed on a computer having a dedicated hardware structure (e.g. the universal computer 1200 shown in FIG. 14) from a memory medium or network, and the computer, when installed with various programs, is capable of realizing the functions of these programs.

Figure 14:
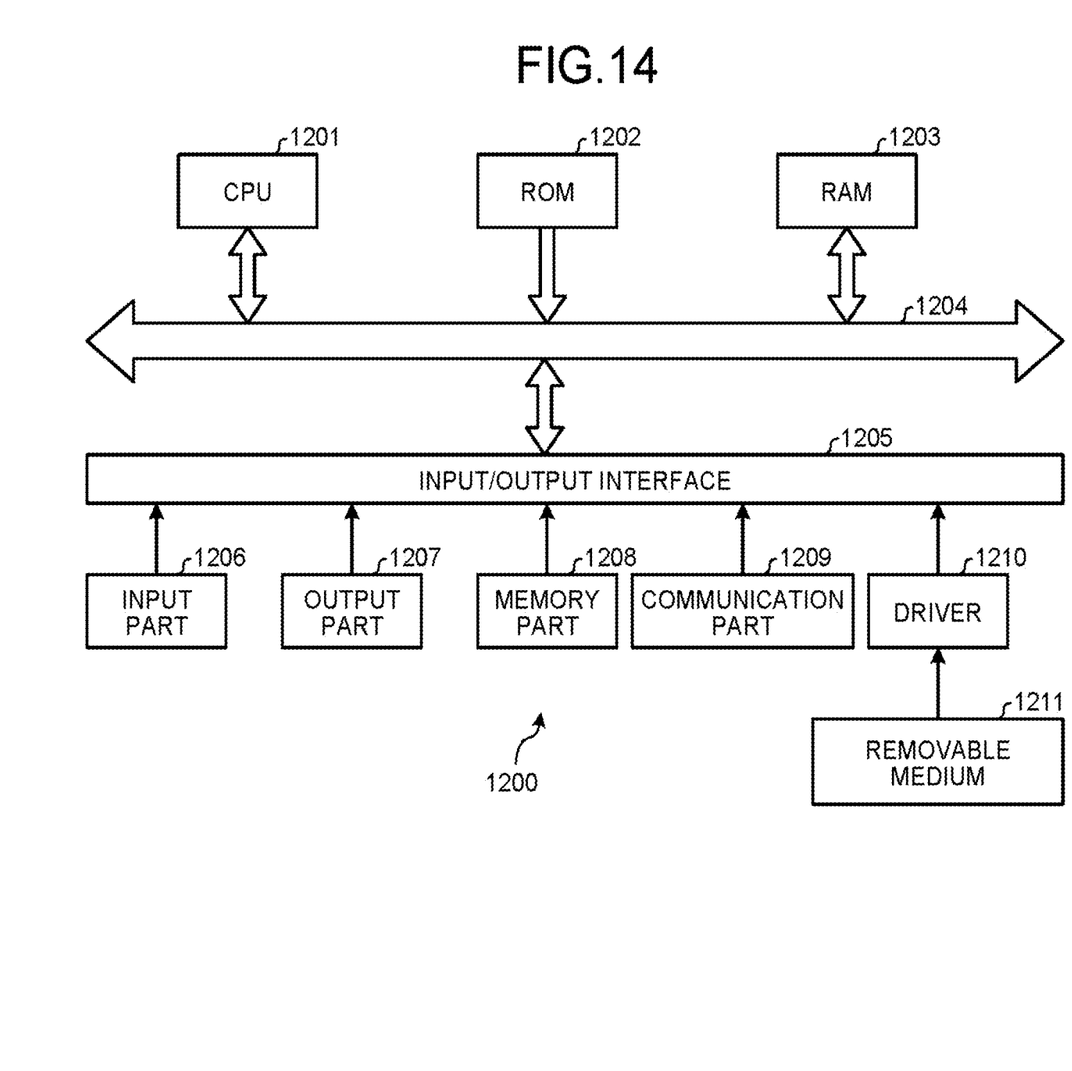
FIG. 14 is a block diagram exemplifying the structure of a computer for realizing embodiments/examples of the present invention.

FIG. 14 is a block diagram exemplifying the structure of a computer for realizing embodiments/examples of the present invention. In FIG. 14, a Central Processing Unit (namely, CPU) 1201 executes various processing according to a program stored in a Read-Only Memory (ROM) 1202 or a program loaded to a Random Access Memory (RAM) 1203 from a memory part 1208. The data needed by the CPU 1201 to execute various processing may be stored in the RAM 1203, if needed. The CPU 1201, the ROM 1202 and the RAM 1203 are linked with each other via a bus line 1204 with which an input/output 1205 is also connected.

The following components are linked with the input/output interface 1205: an input part 1206 (including keyboard, mouse and the like), an output part 1207 (including displays such as cathode ray tube (CRT), liquid crystal display (LCD) and loudspeaker), the memory part 1208 (including hard disk and the like) and a communication part 1209 (including a network interface card such as LAN card and modem). The communication part 1209 carries out a communication processing via a network such as the Internet. A driver 1210 may also be linked with the input/output interface 1205, if needed. If needed, a removable medium 1211, for example, a magnetic disc, an optical disc, a magnetic optical disc, a semiconductor memory and the like, may be installed in the driver 1210 to read a computer program therefrom and install the read computer program in the memory part 1208 as needed.

In the case where the foregoing series of processing is achieved through software, programs forming the software are installed from a network such as the Internet or a memory medium such as the removable medium 1211.

It should be appreciated by those skilled in the art that the memory medium is not limited to the removable mediums 1211 shown in FIG. 14 in which programs are stored and which are distributed separated from the apparatus to provide the programs for users. The removable medium 1211 may be, for example, a magnetic disc (including floppy disc (registered trademark)), a compact disc (including compact disc read-only memory (CD-ROM) and digital video disk (DVD)), a magnetic optical disc (including mini disc (MD) (registered trademark)), and a semiconductor memory. Alternatively, the memory mediums may be the hard discs included in the ROM 1202 and the memory part 1208, and programs are stored in the memory mediums and can be distributed to users along with the memory medium.

The present invention further provides a program product in which machine-readable instruction codes are stored. The data processing methods according to the foregoing embodiments of the present invention can be executed when the instruction codes are read and executed by a machine.

Accordingly, a storage medium for storing the program product in which computer-readable instruction codes are stored is also included in the present invention. The storage medium includes, but is not limited to, a soft disc, an optical disc, a magnetic optical disc, a memory card, a memory stick and the like.

In the foregoing description of specific embodiments of the present invention, the features described and/or shown for an implementation mode may be used in one or more other implementation modes in the same or like way or combined with those of the other implementation modes, or replace those of the other implementation modes.

It should be emphasized that the terms 'comprise/include', as used herein, refer to the presence of a feature, an element, a step or a component but do not preclude the presence or addition of one or more other features, elements, steps or components.

In the above-described embodiments and examples, each step and/or unit are/is represented with a reference sign consisting of figures. It should be understood by those of ordinary skill in the art that the reference signs are merely intended to facilitate description and drawing but are not to be construed as limiting an order or any other aspect.

Furthermore, the methods of the present invention may be implemented sequentially, synchronously or independently according to another time sequence, but not limited to being implemented according to the time sequence described herein. Therefore, the implementation order of the methods described herein is not to be construed as limiting the technical scope of the present invention.

While the present invention has been disclosed with reference to descriptions for the specific embodiments of the present invention, it should be understood that all of the above mentioned embodiments and examples are illustrative instead of limiting. A variety of modifications, improvements or equivalents can be devised by those skilled in the art without departing from the spirit and scope of the present invention. The modifications, improvements or equivalents should also be considered as being included in the protection scope of the present invention.

Through the foregoing description, embodiments of the present invention also provide the following technical solutions:

Appendix 1. A data processing apparatus for processing medical image data, comprising:

a data loading unit configured to load data of one or more voxels obtained by scanning a specific part of an object body;

a change detection unit configured to detect, by performing a comparison using a characteristic parameter obtained from the data, a voxel undergoing a change which refers to that the difference of the characteristic parameter and a reference value exceeds a predetermined degree; and a change presentation unit configured to indicate a position of the voxel undergoing the change and a degree of the change to a user through a display.

Appendix 2. The data processing apparatus according to appendix 1, wherein the reference value includes at least one of: an empirical value, a corresponding value of a symmetric voxel and a historical value of the symmetric voxel.

Appendix 3. The data processing apparatus according to appendix 2, wherein the change detection unit comprises an empirical value comparison module configured to compare the obtained characteristic parameter with the empirical value which is set in advance.

Appendix 4. The data processing apparatus according to appendix 2, wherein the change detection unit comprises:

a position matching module configured to obtain, aiming at a voxel, a voxel symmetrical in position to the voxel; and a symmetry comparison module configured to compare characteristic parameters of the two voxels to determine whether or not one of the voxels undergoes the change.

Appendix 5. The data processing apparatus according to any one of appendixes 1-4, further comprising:

a historical data loading unit configured to load historical data of a voxel stored aiming at a specific part of the same object body; and a scan planning unit configured to set a position to be scanned currently and scanning parameters according to the historical data, wherein the current data loaded by the data loading unit is obtained by scanning the specific part of the object body according to the position to be scanned and the scanning parameters.

Appendix 6. The data processing apparatus according to appendix 5, further comprising:

a trend determination unit configured to determine a change trend of the characteristic parameter of each voxel with time based on the current data loaded by the data loading unit and the historical data.

Appendix 7. The data processing apparatus according to appendix 5, wherein the scan planning unit comprises:

a pre-scanning module configured to pre-scan the object body to obtain a scan location map; and a registration module configured to perform a registration on the scan location map and the historical data to unify the position to be scanned currently and the scanned position in the historical data.

Appendix 8. The data processing apparatus according to any one of appendixes 1-4, wherein the characteristic parameter includes at least one of: a metabolic concentration of a metabolite, a peak height of a spectral line of the metabolite and relative values to metabolic concentrations of other metabolites or relative values to the peak heights of spectral lines of other metabolites Appendix 9. The data processing apparatus according to appendix 2 or 3, wherein the empirical value is related to at least one of the specific part, a scanning sequence, a race of the object and an age of the object and is obtained from a pre-trained database.

Appendix 10. The data processing apparatus according to any one of appendixes 1-4, wherein the degree of the change is defined by a mean and variance of the characteristic parameter.

Appendix 11. The data processing apparatus according to any one of appendixes 1-4, wherein the change presentation unit is configured to indicate the degree of the change using darkness of a color and indicate different metabolites using different colors if there are characteristic parameters of a plurality of metabolites.

Appendix 12. The data processing apparatus according to any one of appendixes 1-4, further comprising:

a user selection unit configured to select one or more voxels through an input of the user; and a detail display unit configured to display information related to the characteristic parameter of the one or more selected voxels.

Appendix 13. A medical imaging device, comprising: the data processing apparatus of any one of appendixes 1-12.

Appendix 14. The medical imaging device according to appendix 13, wherein the medical imaging device is a magnetic resonance imaging device.

Appendix 15. A data processing method for processing medical image data, comprising:

loading data of one or more voxels obtained by scanning a specific part of an object body;

detecting, by performing a comparison using a characteristic parameter obtained from the data, a voxel undergoing a change which refers to that the difference of the characteristic parameter and a reference value exceeds a predetermined degree; and indicating a position of the voxel undergoing the change and a degree of the change to a user through a display.

Appendix 16. The data processing method according to appendix 15, wherein the reference value includes at least one of: an empirical value, a corresponding value of a symmetric voxel and a historical value of the symmetric voxel.

Appendix 17. The data processing method according to appendix 16, wherein the comparison comprises comparing the obtained characteristic parameter with the empirical value which is set in advance.

Appendix 18. The data processing method according to appendix 16, wherein detecting a changed voxel comprises:

obtaining, aiming at a voxel, a voxel symmetrical in position to the voxel; and comparing characteristic parameters of the two voxels to determine whether or not one of the voxels undergoes the change.

Appendix 19. The data processing method according to any one of appendixes 15-18, further comprising:

loading historical data of a voxel stored aiming at a specific part of the same object body; and setting the position to be scanned currently and scanning parameters according to the historical data, wherein the current data loaded is obtained by scanning the specific part of the object body according to the position to be scanned and the scanning parameters.

Appendix 20. The data processing method according to appendix 19, further comprising:

determining a change trend of the characteristic parameter of each voxel with time based on the loaded current data and the historical data.

Appendix 21. The data processing method according to appendix 19, wherein setting the position to be scanned currently and scanning parameters according to the historical data comprises:

pre-scanning the object body to obtain a scan location map; and performing a registration on the scan location map and the historical data to unify the position to be scanned currently and the scanned position in the historical data.

Appendix 22. The data processing method according to any one of appendixes 15-18, wherein the characteristic parameter includes at least one of: a metabolic concentration of a metabolite, a peak height of a spectral line of the metabolite and relative values to metabolic concentrations of other metabolites or relative values to the peak heights of spectral lines of other metabolites Appendix 23. The data processing method according to appendix 16, wherein the empirical value is related to at least one of the specific part, a scanning sequence, a race of the object and an age of the object and is obtained from a pre-trained database.

Appendix 24. The data processing method according to any one of appendixes 15-18, wherein the degree of the change is defined by a mean and variance of the characteristic parameter.

Appendix 25. The data processing method according to any one of appendixes 15-18, wherein indicating the position of a changed voxel and the degree of the change comprises: indicating the degree of the change using darkness of a color and indicating different metabolites using different colors if there are characteristic features of a plurality of metabolites.

Appendix 26. The data processing method according to any one of appendixes 15-18, further comprising:
selecting one or more voxels through an input of the user; and displaying information related to a characteristic parameter of the one or more selected voxels.

Appendix 27. A computer program for realizing the data processing method of any one of appendixes 15-26.

Appendix 28. A computer-readable recording medium on which computer program codes for realizing the data processing method of any one of appendixes 15-26 are recorded.

What is claimed is:

1. A medical information processing apparatus, comprising:

determination circuitry configured to determine whether there is a change in an amount of individual metabolites among a plurality of metabolites in magnetic resonance spectroscopy within a common target region set on medical image data by comparing the amount of each of the plurality of metabolites with a reference value corresponding to each metabolite; and display control circuitry configured to display, within the common target region, a plurality of different colors corresponding to respective ones of a plurality of measurement results, each of the plurality of measurement results indicating whether the amount of each of the plurality of metabolites is changed.

2. The medical information processing apparatus according to claim 1, wherein the determination circuitry determines a degree of the change in the amount of each of the plurality of metabolites; and the display control circuitry displays information including the degree of the change in the amount of each of the plurality of metabolites, as each of the plurality of measurement results.

3. The medical information processing apparatus according to claim 2, wherein the determination circuitry determines the degree of the change by using mean and variance of the amount of each of the plurality of metabolites.

4. The medical information processing apparatus according to claim 2, wherein the display control circuitry displays the degree of the change by shades of a color.

5. A medical information processing device according to claim 4, wherein the display control circuitry displays images of explanatory notes representing a correspondence relationship between colors and each of the plurality of metabolites.

6. The medical information processing apparatus according to claim 1, wherein the determination circuitry determines whether there is a change in the amount of each of the plurality of metabolites in a plurality of target regions; and the display control circuitry displays the plurality of measurement results by associating therewith each of the plurality of the target regions.

7. The medical information processing apparatus according to claim 1, wherein the reference value comprises at least one of: an empirically obtained empirical value, a corresponding value corresponding to a region symmetrical in position to the target region, and a previously obtained historical value.

8. The medical information processing apparatus according to claim 7, wherein the determination circuitry compares the amount of each of the plurality of metabolites with the empirical value which is set in advance.

9. The medical information processing apparatus according to claim 7, wherein the determination circuitry obtains as the corresponding value, information on the plurality of metabolites included in the region symmetrical in position to the target region, and compares the obtained corresponding value with each of the plurality of metabolites.

10. The medical information processing apparatus according to claim 7, wherein the empirical value corresponds to at least one of a specific part, a scanning sequence, a race of an object, and an age of the object, and is obtained from a pre-trained database.

11. The medical information processing apparatus according to claim 1, further comprising:

obtaining circuitry configured to obtain information on stored historical medical image data of an object body corresponding to the medical image data; and setting circuitry configured to set an image capture condition and the target region in accordance with the information on the historical medical image data.

12. The medical information processing apparatus according to claim 11, further comprising:

specifying circuitry configured to specify a change trend in an amount of the plurality of metabolites in accordance with the medical image data and the information on the historical medical image data.

13. The medical information processing apparatus according to claim 11, wherein the setting circuitry performs registration on a location image captured by pre-scanning and the historical medical image data to set, as the image capture condition, a scanning range of a position corresponding to a scanning range of the historical medical image data.

14. The medical information processing apparatus according to claim 1, wherein the amount of each of the plurality of metabolites includes at least one of a metabolic concentration of each metabolite, a peak value of the magnetic resonance spectroscopy, and relative values with respect to the metabolic concentrations of other metabolites or the peak value.

15. The medical information processing apparatus according to claim 1, wherein the display control circuitry displays an image of lines representing a position and a shape of the target region on the medical image data.

16. The medical information processing device according to claim 1, further comprising a receiving circuitry configured to receive instructions from an operator to select the target region, wherein the display control circuitry displays information on the plurality of metabolites in the target region selected in accordance with the instructions.

17. A medical imaging diagnostic device, comprising:
   determination circuitry configured to determine whether there is a change in an amount of individual metabolites among a plurality of metabolites in magnetic resonance spectroscopy within a common target region set on the medical image data by comparing the amount of each of the plurality of metabolites with a reference value corresponding to each metabolite; and
   display control circuitry configured to display, within the common target region, a plurality of different colors corresponding to respective ones of a plurality of measurement results, each of the plurality of measurement results indicating whether the amount of each of the plurality of metabolites is changed.

18. The medical imaging diagnostic device according to claim 17, wherein the medical imaging diagnostic device is a magnetic resonance imaging device.

19. A method for processing medical information, comprising:
   determining whether there is a change in an amount of individual metabolites among a plurality of metabolites in magnetic resonance spectroscopy within a common target region set on the medical image data by comparing the amount of each of the plurality of metabolites with a reference value corresponding to each metabolite; and
   displaying within the common target region a plurality of different colors corresponding to respective ones of a plurality of measurement results, each of the plurality of measurement results indicating whether the amount of each of the plurality of metabolites is changed.

* * * * *